US005610057A

United States Patent [19]

Shen et al.

[11] Patent Number: 5,610,057
[45] Date of Patent: Mar. 11, 1997

[54] MONOCLONAL ANTIBODY SPECIFIC FOR IGA RECEPTOR

[75] Inventors: Li Shen, Thetford Center, Vt.; Michael W. Fanger, Lebanon, N.H.

[73] Assignee: Medarex, Inc., Annandale, N.J.

[21] Appl. No.: 222,572

[22] Filed: Apr. 4, 1994

Related U.S. Application Data

[63] Continuation of Ser. No. 871,561, Apr. 16, 1992, abandoned, which is a continuation of Ser. No. 424,883, Oct. 20, 1989, abandoned.

[51] Int. Cl.$^6$ .............................. C12N 5/20; C07K 16/28
[52] U.S. Cl. ...................................... 435/334; 530/388.22
[58] Field of Search ................ 530/388.22; 435/240.27, 435/70.21, 172.2

[56] References Cited

U.S. PATENT DOCUMENTS 4,676,980  6/1987  Segal et al. .
4,954,617  9/1990  Fanger et al. .

OTHER PUBLICATIONS

Hook et al. Fed Proc 42:713, 1983.
Anderson et al. J. Biol. Chemistry 261(27):12856–12864 1980.
Fanger et al. Molecular Immunology 20(9):1019–1027, 1983.
Harris et al. Fibtech 11:42–44, 1993.
Shen et al., *J. Immunol.* 137:3378–3382 (1986).
Karpovsky et al., *J. Exp. Med.* 160:1686–1701 (1984).
Shen, L. et al. *J. Immunol.* 143(12):4117–4122 (1989).
Tokumoto, H. et al. *Monogr. Allergy* 24:208–214 (1988).
Albrechtsen, M. et al. *Immunology* 64:201–205 (1988).
Monteiro, R.C. et al. *Faseb J.* 3:A110 (1989).
Shen, L. and Collins, J. *Immunology* 68:491–496 (1989).
Chevailler, A. et al. *J. Immunol.* 142(7):2244–2249 (1989).

*Primary Examiner*—Paula K. Hutzell
*Attorney, Agent, or Firm*—Lahive & Cockfield; Giulio A. DeConti, Jr.; Beth E. Arnold, Esq.

[57] ABSTRACT

Monoclonal antibodies which react specifically to Fc receptor for IgA of human effector cells, such as monocytes, polymorphonuclear cells and macrophages, are disclosed.

2 Claims, No Drawings

5,610,057

MONOCLONAL ANTIBODY SPECIFIC FOR IGA RECEPTOR

This application is a continuation of application Ser. No. 07/871,561, filed on Apr. 16, 1992 (abandoned) which is a continuation of application Ser. No. 07/424,883 filed on Oct. 20, 1989 (abandoned).

BACKGROUND

Receptors for the Fc portion of immunoglobulin are important in triggering many of the protective functions of monocytes, macrophages and polymorphonuclear cells. While receptors for IgG on these cells have been extensively investigated, it is becoming evident that receptors for IgA are also capable of promoting effector functions of these cells and that IgE may stimulate some activities of monocytes. While soluble IgA binds IgA receptor with poor avidity, polymerized IgA has been demonstrated to trigger functions such as superoxide generation and phagocytosis.

SUMMARY OF THE INVENTION

This invention pertains to a monoclonal antibody which specifically binds to Fc receptor for IgA (Fc-alpha receptor) on effector cells such as a monocytes, polymorphonuclear cells and macrophages and which can trigger Fc-alpha-receptor-mediated effector function. The antibody (or fragment thereof) can be linked (chemically or genetically) to an antibody (or fragment thereof) specific for a target antigen to form a bispecific antibody or heteroantibody. These bispecific molecules can be used to direct effector cells to cells bearing the target antigen, resulting in cytolysis of the cell.

DETAILED DESCRIPTION OF THE INVENTION

The antibody of this invention binds the Fc-alpha receptor (FcRI) for human IgA. The monoclonal anti-Fc-alpha receptor antibody of this invention can be produced by conventional monoclonal antibody methodology e.g., the standard somatic cell hybridization technique of Kohler and Milstein, *Nature* 256: 495 (1975). Although somatic cell hybridization procedures are preferred, in principle, other techniques for producing monoclonal antibody can be employed e.g., viral or oncogenic transformation of B lymphocytes.

Human cells bearing Fc-alpha receptor can be used to immunize an animal for production of monoclonal antibody. Alternatively, the receptor for immunization of an animal can be prepared from lysates of human cells which express the receptor, e.g., a human monocytic cell. In another mode, a partially purified preparation of the receptor can be made by lysing receptor-bearing cells and then purifying the receptor by immunoadsorbant chromatography. Cells can be lysed in a buffer containing a detergent such as NP40. The immunoadsorbent can be prepared by attaching human IgA to a water-insoluble material such as an activated Sepharose™ resin. The Sepharose resin with attached human IgA is poured into a column. The cell lysate is passed through the column under conditions which permit absorption of the cellular Fc receptor protein by the IgA coupled to the resin. The adsorbed Fc receptor protein can be eluted with a mildly acidic elution buffer. The purified receptor can then be used for immunization of an animal to produce anti-receptor monoclonal antibody.

The preferred animal system for preparing hybridomas is the murine system. Hybridoma production in the mouse is a very well-established procedure. Immunization protocols and techniques for isolation of immunized splenocytes for fusion are well known in the art. Fusion partners (e.g., murine myeloma cells) and fusion procedures are also well-known.

Employing the methodology described, a monoclonal antibody (mAb) My 43 of the IgM class was produced which binds specifically to monocyte and polymorphonuclear cell IgA receptors, based on its ability to block IgA mediated rosettes and phagocytosis. This antibody recognizes a surface molecule which triggers function since monocytes and PMNs secrete superoxide when treated with this antibody.

A hybridoma producing monoclonal anti-human Fc-α receptor My43 was deposited with the American Type Culture Collection (ATCC), Rockville, Md. 20852 on Jun. 12, 1996 and has been assigned ATCC Designation No. HB-12128.

The antibodies of this invention can be used to target effector cells bearing Fc-alpha receptor. To target effector cells, bifunctional antibodies or heteroantibodies are employed. These antibodies have dual antigen binding specificity—one specificity for the Fc-alpha receptor and one specificity for an epitope of the target cell. The Fc receptor specificity mediates linkage to the effector cell through a known cytotoxic trigger molecule. The target cell specificity provides for recognition and binding to the target cell.

Bifunctional antibodies are single, divalent antibodies which have two different antigen binding sites. Bifunctional antibodies for targeting have one binding site for Fc receptor and one binding site for a target cell epitope.

Hetereoantibodies are two or more antibodies or antibody binding fragments (Fab) linked together, each antibody or fragment having a different specificity. Heteroantibodies for targeting comprise an antibody or antigen binding fragment specific for Fc receptor for IgA, coupled to an antibody or antigen binding fragment thereof specific for a target cell epitope.

Bifunctional antibodies can be produced by chemical techniques (see e.g., D. M. Kranz et al., *Proc. Natl. Acad. Sci. USA* 78,5807 (1981)) by "polydoma" techniques (See U.S. Pat. No. 4,474,893, to Reading) or by recombinant DNA techniques. Heteroantibodies can be prepared by conjugating Fc receptor antibody with antibody specific for an epitope of a target cell. A variety of coupling or crosslinking agents can be used to conjugate the antibodies. Examples are protein A, carboiimide, and N-succinimidyl-3-(2-pyridyldithio) propionate (SPDP). SPDP is the preferred agent; procedures for crosslinking antibodies with this agent are known in the art. See e.g., Karpovsky et al., (1984) *J. Exp. Med.* 160:1686; Liu, M. A. et al., (1985) *Proc. Natl. Acad. Sci USA* 82:8648.

Employing the SPDP agent, bi-Specific antibodies of the monoclonal antibody My 43 and Fab anti-erythrocyte antibodies were prepared and shown to promote phagocytosis by monocytes (whereas bi-specific antibodies of anti-RBC x-anti-beta$_2$ microglobulin did not). In comparative studies on phagocytosis, an average of 52% of monocytes ingested IgKG coated red cells and 32% ingested cells coated with My 43 bi-specific antibodies.

Target cells are cells whose elimination would be beneficial to the host. One important type of cell is a tumor cell. Effector cells can be targeted with bi-functional or heteroantibody having specificity for FcRI and specificity for a tumor associated or tumor specific antigen.

Antibodies with a desired tumor specificity for production of bifunctional antibody or heteroantibody can be produced or can be selected from available sources. Monoclonal antibodies against tumor-associated antigens can be made by the methods of Koprowski et al., U.S. Pat. No. 4,172,124. Many suitable anti-cancer antibodies are presently available.

Specific anti-tumor antibodies would include, but not be limited to:

| Antibody | Specificity |
| --- | --- |
| AML-2-23, PM-81, PMN-6, PMN-19 | Myeloid Leukemia |
| SCCL-1, SCCL-175 | Small Cell Carcinoma of the Lung |
| OC1-25, OVCT-3 | Ovarian Carcinoma |
| COL-1, COL-2, COL-3, . . . COL-13 | Colon Carcinoma |

In addition to tumor cells, the effector cell can be targeted against an auto-antibody lymphocyte for treatment of autoimmune disease or an IgE-producing lymphocyte for treatment of allergy. The target can also be microorganism (bacterium or virus) or a soluble antigen (such as rheumatoid factor or other auto-antibodies).

Effector cells for targeting are human leukocytes, preferably macrophages. Other cells would include monocytes and other IgA-receptor bearing cells. If desired, effector cells for targeting can be obtained from the host to be treated.

The targeted effector cells can be administered as a suspension of cells in a physiologically acceptable solution. The number of cells administered can be in the order of $10^8$–$10^9$ but will vary depending on the therapeutic purpose. In general, the amount will be sufficient to obtain localization at the target cell and to effect target cell killing by antibody dependent mediated cytolysis (ADCC). Routes of administration can also vary. In tumor therapy, for instance, depending upon the localization of a tumor, the targeted effector cells could be administered intravenously, or directly into tumor sites; as for example, directly into the peritoneal cavity in the case of ovarian carcinoma.

Therapy with targeted effector cells can be performed in conjunction with other techniques for removal of targeted cells. For example, anti-tumor therapy with bifunctional antibodies and/or effector cells armed with bifunctional (hetero)antibody can be used in conjunction with surgery, chemotherapy or radiotherapy. Additionally, combination immunotherapy may be used to direct two distinct cytotoxic effector populations toward tumor cell rejection. For example, anti-tumor antibodies linked to anti-Fc-gammaRI or anti-T3 (will trigger cytolytic T lymphocytes to lyse tumor cells) may be used in conjunction with IgA-receptor specific heteroantibodies. Protocols based on these concepts may be especially effective in removing residual tumor cells in patients induced into remission by chemotherapy and irradiation.

The anti-Fc-alpha receptor antibody of this invention has additional utility in therapy and diagnosis. The Fc receptor antibody itself can be a targeting antibody (i.e., to target cells bearing Fc-alpha receptor). For example, the antibody can be used to target lipid vesicles containing anticancer drugs for treatment of certain hematological cancers (e.g. acute myeloid leukemia), or to target lipid vesicles containing factors (such as gamma-IFN) which activate monocytes. The antibody, if of the appropriate murine IgG subclass (e.g., IgG2a), can be used directly in vivo to eliminate Fc-alpha-receptor-bearing cells (e.g., myeloid leukemia cells) via natural complement or ADCC mechanisms.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. Hybridoma cell line My43, ATCC accession number HB-12128.

2. An anti-human Fc-α receptor monoclonal antibody, MY43, which is produced by hybridoma cell line, ATCC accession number HB-12128.

* * * * *